United States Patent
Dzhemilev et al.

(10) Patent No.: US 8,530,688 B2
(45) Date of Patent: Sep. 10, 2013

(54) METHOD FOR PREPARING EXO-TRICYCLO[4.2.1.0$^{2,5}$]NON-7-ENE-3-SPIRO-1'-(3'-ETHYL-3'-ALUMINA)CYCLOPENTANE

(75) Inventors: Usein Memetovich Dzhemilev, Ufa (RU); Vladimir Anatolievich Diyakonov, Ufa (RU); Olga Alexandrovna Trapeznikova, Ufa (RU); Iskhat Gabdrakhmanovich Ibragimov, Ufa (RU)

(73) Assignee: Uchrezhdenie Rossiiskoi Akademii Nauk Institut Neftekhimii I Kataliza Ran, Ufa (RU)

( * ) Notice: Subject to any disclaimer, the term of this patent is extended or adjusted under 35 U.S.C. 154(b) by 0 days.

(21) Appl. No.: 13/320,295

(22) PCT Filed: May 13, 2010

(86) PCT No.: PCT/RU2010/000240
§ 371 (c)(1),
(2), (4) Date: Apr. 2, 2012

(87) PCT Pub. No.: WO2010/134849
PCT Pub. Date: Nov. 25, 2010

(65) Prior Publication Data
US 2012/0184761 A1    Jul. 19, 2012

(30) Foreign Application Priority Data
May 18, 2009    (RU) .................... 2009118676

(51) Int. Cl.
*C07F 5/06*    (2006.01)
(52) U.S. Cl.
USPC ........................................... 556/175
(58) Field of Classification Search
USPC ........................................... 556/175
See application file for complete search history.

(56) References Cited

FOREIGN PATENT DOCUMENTS

| RU | 2342392 C2 | 12/2008 |
|---|---|---|
| RU | 2342393 C2 | 12/2008 |
| RU | 2342395 C2 | 12/2008 |

OTHER PUBLICATIONS

D'yakonov, Vladimir A., et al., "Dzhemilev reaction for the synthesis of spiro[3.3]heptane and spiro[3.4] octanes", Science Direct, Tetrahedron Letters 48 (2007), pp. 8583-8586.
Dzhemilev, Usien M., et al., "Zirconium-catalyzed preparation of aluminacyclopentanes and synthesis of five-membered carbo- and heterocycles", Science Direct, Tetrahedron 60 (2004), pp. 1281-1286.
Xi, Zhenfeng, et al., "Deoxygenative Cycloaddition of Aldehydes with Alkynes Mediated by AlCl$_3$ and Zirconium: Formation of Cyclopentadiene Derivatives", Angew. Chem. Int. Ed. 2000, 39, No. 16, pp. 2950-2952.
Dzhemilev, U. M., et al., "Synthesis and transformations of metallocycles 14.* Steroselective synthesis of *trans*-3,4-dialkyltetrahydrothiophenes", Russian Chemical Bulletin, vol. 43, No. 2, Feb. 1994, pp. 255-257.
Dzhemilev, U.M., et al., Synthesis and Conversions of Metallocycles 9.* synthesis of Polycyclic Aluminocyclopentanes With the Participation of (n$^5$-C$_5$H$_5$)$_2$ZrCl$_2$*. Izvestiya Akademii Nauk, Seriya Khimicheskaya, No. 2, Feb. 1992, pp. 386-391.

*Primary Examiner* — Porfirio Nazario Gonzalez
(74) *Attorney, Agent, or Firm* — Ladas & Parry LLP

(57) ABSTRACT

The invention relates to the field of organic synthesis, more specifically to a method for preparing novel organo-aluminum compounds. The compound in question can be used as a component in catalytic systems in processes for the oligomerization and polymerization of olefin, diene and acetylene hydrocarbons as well as in fine organic and organometallic synthesis. The essence of the method consists in reacting 3-methylene-exo-tricyclo[4.2.1.0$^{2,5}$]non-7-ene with triethylaluminium in the presence of the catalyst zirconocene dichloride in an inert gas atmosphere, preferably in argon or nitrogen, at room temperature, in an aliphatic or aromatic solvent for 5-7 h.

7 Claims, No Drawings

METHOD FOR PREPARING EXO-TRICYCLO[4.2.1.0²,⁵]NON-7-ENE-3-SPIRO-1'-(3'-ETHYL-3'-ALUMINA)CYCLOPENTANE

FIELD OF THE INVENTION

The invention relates to methods of obtaining new aluminum-organic compounds, specifically to the method of obtaining exo-tricyclo[4.2.1.0²,⁵]non-7-en-3-spiro-1'-(3'-ethyl-3'alumina)cyclopentane of the general formula (1):

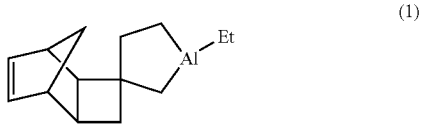

(1)

The compound can find application as a component in the catalyst systems in processes of oligo- and polymerization of olefinic, diene, and acetylenic hydrocarbons (Yu. B. Monakov, G. A. Tolstikov, *Catalytic polymerization of 1,3-dienes*, Nauka, Moscow, 1990, 211 pp.) and also in fine organic and metallo-organic syntheses for obtaining carbo- and heterocyclic N-, S-, Se-, Si-, P-, and O-containing compounds with the spiran structure (V. A. D.'yakonov, E. Sh. Finkelshtein, A. G. Ibragimov, *Tetrahedron Lett.*, 2007, 48, 8583; U. M. Dzhemilev, A. G. Ibragimov, R. R. Gilazev, L. O. Khafizova, *Tetrahedron Lett.*, 2004, 60, 1281; Z. Xi, P. Li, *Angew. Chem. Int. Ed.*, 2000, 39, 2950; U. M. Dzhemilev, A. G. Ibragimov, R. R. Muslukhov, *Izv. AN, Ser. Khim.*, 1994, 276).

BACKGROUND ART

The prior art (U. M. Dzhemilev, A. G. Ibragimov, A. P. Zolotarev, L. M. Khalilov, R. R. Muslukhov, *Synthesis and conversion of metallocycles. Synthesis of polycyclic alumacyclopentanes involving (η⁵-C₅H₅)₂ZrCl₂. Izv. AN, Ser. Khim.*, 1992, no. 2, pp. 386-391) relates to a method of obtaining tricyclic AOC, specifically, 3-ethyl-3-alumatricyclo[5.2.1.0²,⁵]decane (2) by a reaction of norbornen with triethylaluminum (Et₃Al) under the action of a catalyst zirconacendichloride (Cp₂ZrCl₂) in hydrocarbon solvents at a temperature of ~25° C. for 12 to 14 hours in accordance with the scheme:

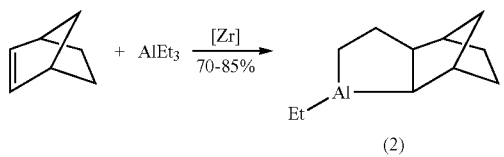

(2)

The method is insufficient for obtaining exo-tricyclo[4.2.1.0²,⁵]non-7-en-3-spiro-1'-(3'-ethyl-3'alumina)cyclopentane of the general formula (1).

The prior art (U. M. Dzhemilev, A. G. Ibragimov, A. P. Zolotarev, L. M. Khalilov, R. R. Muslukhov, *Synthesis of polycyclic alumacyclopentanes involving (Cp₂ZrCl₂. Izv. AN, Ser. Khim.*, 1992, no. 2, pp. 386) relates to a method of obtaining tri- and tetracyclic AOC, specifically, 3-ethyl-3-aluminatricyclo[5.2.1.0²,⁶]dec-8-en (3) and 3,9-diethyl-3,9-dialuminatetracyclo[5.5.1.0²,⁶.0⁸,¹²]tridecane (4) at a ratio of ~2:8 with the integrated yield ~75% by a reaction of norbornadiene en with triethylaluminum taken at a mole ratio of 1:2 in the presence of 3 to 5 mol % of Cp₂ZrCl₂ at a temperature of ~20° C. for 12-14 hours in accordance with the scheme:

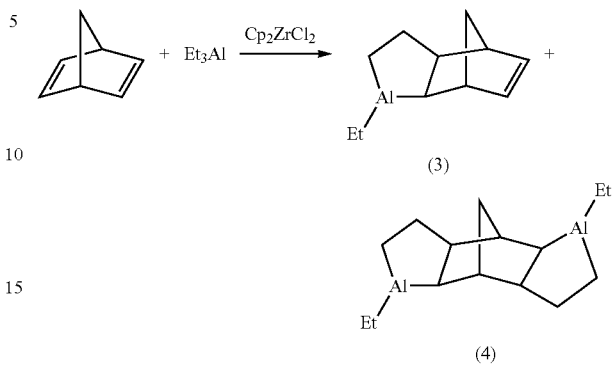

The method is insufficient for obtaining exo-tricyclo[4.2.1.0²,⁵]non-7-en-3-spiro-1'-(3'-ethyl-3'alumina)cyclopentane of the general formula (1).

Thus there are no published data on the synthesis of exo-tricyclo[4.2.1.0²,⁵]non-7-en-3-spiro-1'-(3'-ethyl-3'alumina)cyclopentane of the general formula (1).

DISCLOSURE OF THE INVENTION

This invention relates to a method of regioselective synthesis of exo-tricyclo[4.2.1.0²,⁵]non-7-en-3-spiro-1'-(3'-ethyl-3'alumina)cyclopentane of the general formula (1).

The essence of the invention is the reaction of 3-methylene-exo-tricyclo[4.2.1.0²,⁵]non-7-en with triethylaluminum (Et₃Al) in the presence of catalyst zirconacendichloride (Cp₂ZrCl₂) taken at a mole ratio of 3-methylene-exo-tricyclo[4.2.1.0²,⁵]non-7-en:Et₃Al:Cp₂ZrCl₂=10:(10-14):(0.6-1.0), preferably, 10:12:0.8. The reaction is carried out in an atmosphere of inert gas, preferably, argon or nitrogen at room temperature (~20° C.) and atmospheric pressure in an aliphatic or aromatic solvent, preferably, pentane, hexane, octane, benzene, or toluene. The reaction is impossible in ether (ether, dioxane) or halogenated (methylene chloride) solvents. The optimum reaction time is 5 to 7 hours, with the yield of the target product being 69-81%. A reduction of the reaction time is associated with a reduction of the target product yield.

The reaction proceeds in accordance with the scheme:

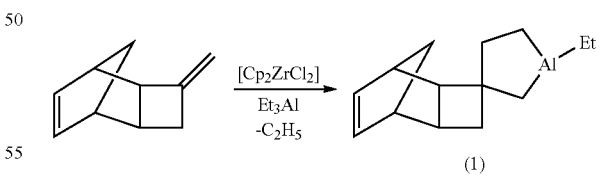

(1)

The target product (1) is formed only if the starting reagents are 3-3-methylene-exo-tricyclo[4.2.1.0²,⁵]non-7-en, Et₃Al, and catalyst Cp₂ZrCl₂. In the presence of other olefins (e.g., 4-vinylcyclohex-1-en, methylene alkanes, and cycloolefines), other aluminum compounds (e.g., EtAlCl₂, iso-Bu₃Al, iso-Bu₃AlCl, iso-Bu₂AlH) or other transition metal complexes (e.g., Zr(acac)₄, Cp₂TiCl₂, Pd(acac)₂, Ni(acac)₂, Fe(acac)₃) the target product is not formed.

The reaction carried out in the presence of catalyst Cp₂ZrCl₂ in a ratio of more than 10 mol % in relation to 3-methylene-exo-tricyclo[4.2.1.0$^{2,5}$]non-7-en does not lead to a significant increase in the yield of the target product (1). The use of catalyst Cp$_2$ZrCl$_2$ in a ratio of less than 6 mol % leads to decreasing the yield of the tetracyclic aluminum-organic compound (1) due to the reduction of catalytically active sites in the reacting mass. The experiments were performed at room temperature of ~20° C. At a higher temperature (e.g., 50° C.), the power inputs and the content of compaction products are increasing; at a lower temperature (e.g., 0° C.), the reaction rate decreases.

A change in the starting products ratio towards an increase in the amount of Et$_3$Al in relation to 3-methylene-exo-tricyclo[4.2.1.0$^{2,5}$]non-7-en does not lead to a significant increase in the yield of the target product (1). A decrease in the amount of Et$_3$Al in relation to 3-methylene-exo-tricyclo[4.2.1.0$^{2,5}$]non-7-en leads to a decrease in the yield of the aluminum-organic compound (1).

The Substantial Distinctions of the Proposed Method

The proposed method is based on the use of 3-methylene-exo-tricyclo[4.2.1.0$^{2,5}$]non-7-en as the starting unsaturated compound; with the target product being tetracyclic spiroalane (1). In the prior art method they use norbornadiene as the starting reagent; with the target products being a mixture of an unsaturated tricyclic aluminum-organic compound (3) and a tetracyclic dialuminum compound (4).

The Proposed Method has the Following Advantages:

1. The method permits obtaining with a high regioselectivity an individual exo-tricyclo[4.2.1.0$^{2,5}$]non-7-en-3-spiro-1'-(3'-ethyl-3'alumina)cyclopentane of the general formula (1), the synthesis of which had not been so far reported on.
2. The reaction is performed under mild conditions under normal atmospheric pressure and at room temperature.

EXAMPLES OF EMBODIMENT OF THE METHOD

Example 1

2 ml of hexane, 0.8 mmol of Cp$_2$ZrCl$_2$, and 10 mmol of 3-methylene-exo-tricyclo[4.2.1.0$^{2,5}$]non-7-en were placed into a 50 ml glass reactor installed in a magnetic stirrer in argon atmosphere and mixed thoroughly with 12 mmol of Et$_3$Al at a temperature of ~0° C. for 6 hours. The obtained product is an individual exo-tricyclo[4.2.1.0$^{2,5}$]non-7-en-3-spiro-1'-(3'-ethyl-3'alumina)cyclopentane (1) with the yield of 76%. The yield of the target product was determined with respect of a product of deuterolysis. The deuterolysis of AOC (1) results in the formation of 3-(2-deuteroethyl)-3-(deuteromethyl)-tricyclo[4.2.1.0$^{2,5}$]non-7-en (5)

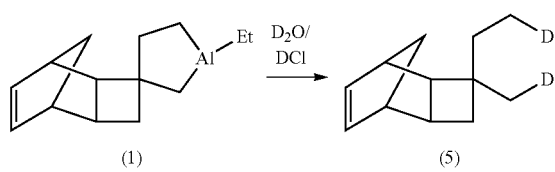

The spectral properties of the deuterolysis product (5)

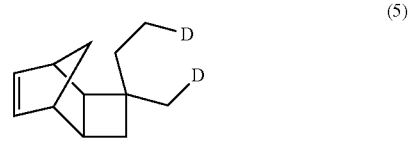 [SMILES: [2H]CCC1(C[2H])CC2C3C=CC(C3)C21]

are as follows.

The NMR$^1$H spectrum (δ, ppm) of 3-(2-deuteroethyl)-3-(deuteromethyl)-tricyclo[4.2.1.0$^{2,5}$]non-7-en (5): 5.98 (m, 2H), 2.65 w.s., 1H), 2.61 (w.s., 1H), 1.80 (d, J=9 Hz, 1H), 1.64 (d.d., J=8 Hz, J=12 Hz, 1H), 1.47 (m., 4H), 1.26 (d., J=9 Hz, 1H), 1.08 (d.d., J=8 Hz, J=12 Hz, 1H), 0.86 (s., 2H), 0.82 (t., J=7 Hz, 2H);

The NMR$^{13}$C spectrum (δ, ppm, J/Hz): 136.2, 135.7, 46.5, 43.3, 41.9, 41.8, 37.5, 37.3, 32.4, 31.9, 17.6 (t., J$_{CD}$=19 Hz), 8.1 (t., J$_{CD}$=19 Hz).

Examples 2-12 were carried out by analogy with Example 1 by varying the reagents ratios, solvents, temperature and time of the reaction.

The reaction was performed under normal atmospheric pressure.

Conditions of the reaction illustrated in Examples 1-12 and the yield of the target product are depicted in Table 1.

TABLE 1

| I-tem | Mole ratio 3-methylene-3-exo-tricyclo-exo-tricyclo-4.2.1.0$^{2,5}$]non-7-en:Et$_3$Al:Cp$_2$ZrCl$_2$, mmol | Solvent | Inert gas | Temperature, °C. | Reaction time, h | YIELD (1), % |
|---|---|---|---|---|---|---|
| 1 | 10:12:0.8 | Hexane | Argon | 20 | 6 | 76 |
| 2 | 10:14:0.8 | Hexane | Argon | 20 | 6 | 78 |
| 3 | 10:10:0.8 | Hexane | Argon | 20 | 6 | 73 |
| 4 | 10:12:1.0 | Hexane | Argon | 20 | 6 | 81 |
| 5 | 10:12:0.6 | Hexane | Argon | 20 | 6 | 69 |
| 6 | 10:12:0.8 | Hexane | Argon | 20 | 7 | 80 |
| 7 | 10:12:0.8 | Hexane | Argon | 20 | 5 | 71 |
| 8 | 10:12:0.8 | Hexane | Argon | 0 | 24 | 58 |
| 9 | 10:12:0.8 | Hexane | Argon | 50 | 5 | 74 |
| 10 | 10:12:0.8 | Pentane | Argon | 20 | 6 | 75 |
| 11 | 10:12:0.8 | Heptane | Argon | 20 | 6 | 76 |
| 12 | 10:12:0.8 | Octane | Argon | 20 | 6 | 76 |
| 13 | 10:12:0.8 | Benzene | Argon | 20 | 6 | 77 |
| 14 | 10:12:0.8 | Toluene | Argon | 20 | 6 | 80 |
| 15 | 10:12:0.8 | Hexane | Nitrogen | 20 | 6 | 75 |

The invention claimed is:

1. A method of obtaining exo-tricyclo[4.2.1.0$^{2,5}$]non-7-en-3-spiro-1'-(3'-ethyl-3' alumina)cyclopentane of the general formula (1):

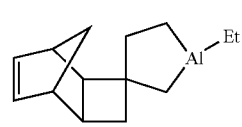

characterized in that 3-methylene-exo-tricyclo[4.2.1.0$^{2,5}$]non-7-en is subjected to the reaction with triethylaluminum (Et$_3$Al) in the presence of catalyst zirconacendichloride (Cp$_2$ZrCl$_2$) in an aliphatic or aromatic solvent in an inert atmosphere.

2. The method according to claim 1, wherein the reaction is carried out at a mole ratio of 3-methylene-exo-tricyclo[4.2.1.0$^{2,5}$]non-7-en:Et$_3$Al:Cp$_2$ZrCl$_2$=10:(10-14):(0.6-1.0).

3. The method according to claim 1, wherein the aliphatic solvent is selected from the group consisting of pentane, hexane, and octane.

4. The method according to claim 1, wherein the aromatic solvent is selected from the group consisting of benzene and toluene.

5. The method according to claim 1, wherein the reaction is carried out in an argon or nitrogen atmosphere.

6. The method according to claim 1, wherein the reaction is carried out at room temperature and under normal atmospheric pressure.

7. The method according to claim 1, wherein the reaction is carried out for 5 to 7 hours.

* * * * *